United States Patent [19]

Farnham et al.

[11] Patent Number: 4,621,125

[45] Date of Patent: Nov. 4, 1986

[54] TRIS(DISUBSTITUTED AMINO)SULFONIUM PERFLUOROALKOXIDES AND -PERFLUOROALKYLMERCAPTIDES AND PROCESS FOR THEIR PREPARATION

[75] Inventors: William B. Farnham, Wilmington, Del.; William J. Middleton, Chadds Ford, Pa.

[73] Assignee: E. I. Du Pont de Nemours and Company, Wilmington, Del.

[21] Appl. No.: 754,140

[22] Filed: Jul. 12, 1985

Related U.S. Application Data

[62] Division of Ser. No. 618,736, Jun. 8, 1984.

[51] Int. Cl.$^4$ ............................ C08F 4/16; C08F 2/00
[52] U.S. Cl. .................................. 526/190; 526/329.7; 526/194
[58] Field of Search ............... 526/209, 210, 190, 194

[56] References Cited

U.S. PATENT DOCUMENTS

| | | | |
|---|---|---|---|
| 3,940,402 | 2/1976 | Middleton | 564/102 |
| 4,414,372 | 11/1983 | Farnham et al. | 526/262 |
| 4,417,034 | 11/1983 | Webster | 526/194 |
| 4,508,880 | 4/1985 | Webster | 526/194 |
| 4,524,196 | 6/1985 | Farnham et al. | 526/194 |

OTHER PUBLICATIONS

Young, Fluorine Chemistry Reviews, 1, 359, 389–397, P. Tarrant, ed., M. Dekker, New York, 1967.
Redwood and Willis, Can. J. of Chem., 43, 1893 (1965).
Redwood and Willis, Can. J. of Chem., 45, 389 (1967).
Downs, J. Chem. Soc., 1962, 4361.

*Primary Examiner*—Joseph L. Schofer
*Assistant Examiner*—Peter F. Kulkosky

[57] ABSTRACT

Tris(disubstituted amino)sulfonium perfluoroalkoxides and tris(disubstituted amino)sulfonium perfluoroalkylmercaptides and process for their preparation.

6 Claims, No Drawings

TRIS(DISUBSTITUTED AMINO)SULFONIUM PERFLUOROALKOXIDES AND -PERFLUOROALKYLMERCAPTIDES AND PROCESS FOR THEIR PREPARATION

CROSS-REFERENCE TO RELATED APPLICATION

This is a division of application Ser. No. 618,736 filed June 8, 1984.

BACKGROUND OF THE INVENTION

1. Field of the Invention

This invention relates to sulfonium salts, and more particularly to tris(disubstituted amino)sulfonium perfluoroalkoxides and -perfluoroalkylmercaptides, and to processes for their preparation.

2. Background

Tris(dialkylamino)sulfonium (TAS) salts of the formula $$(R^1R^2N)(R^3R^4N)(R^5R^6N)S^{\oplus}X^{\ominus}$$

wherein each R is $C_1$–$C_{20}$ alkyl having at least two α-hydrogen atoms and X is $(CH_3)_3SiF_2$, Cl, Br, I, CN, NCO, NCS, $NO_2$ or $N_3$ are disclosed in U.S. Pat. No. 3,940,402. The TAS salts are soluble in organic liquids and are useful as polymerization catalysts and as reagents for replacing various groups in organic compounds with the group X.

Redwood and Willis, Can. J. of Chem. 43, 1893 (1965), disclose the trifluoromethoxides $CF_3O^{\ominus}M^{\oplus}$ (M=K, Rb, Cs) which are stable crystalline solids and are prepared by the reversible reaction of carbonyl fluoride and the appropriate metal fluoride. The salts are too insoluble in organic solvents to be characterized in solution. In the Can. J. of Chem. 45, 389 (1967) the same authors disclose the preparation of the higher perfluoro homologs (ethoxides, n-propoxides, isopropoxides, and n-butoxides) by reaction of the metal fluoride with an acyl fluoride or hexafluoroacetone. Spectroscopic evidence indicates that the alkoxides exist in equilibrium concentration with unreacted carbonyl compound in organic solution. No utility is disclosed for the compounds.

Downs, J. Chem. Soc. 1962, 4361, discloses the preparation of $CF_3SAg$ and $(CF_3S)_2Hg$ by the addition of $AgF$ and $HgF_2$, respectively, to $CF_2S$.

Young, Fluorine Chemistry Reviews, 1, 359, 389–397, P. Tarrant, ed., M. Dekker, New York, 1967, discloses reactions of fluoride ion and polyfluoroalkyl anions, including the formation of perfluoroalkoxides and mercaptides. The formation of perfluoroalkoxides is an equilibrium reaction and isolation requires low temperatures to avoid excessive dissociation. The isolated salts are fairly stable but are extremely moisture sensitive. The alkoxides react with alkyl halides to form ethers.

DETAILED DESCRIPTION OF THE INVENTION

For further comprehension of the invention, and of the objects and advantages thereof, reference may be made to the following description and to the appended claims in which the various novel features of the invention are more particularly set forth.

The invention resides in sulfonium salts, and more particularly in alkoxides and mercaptides of the formula

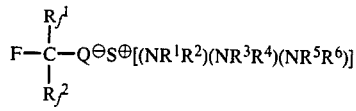

wherein $R^1$ through $R^6$, each selected independently, are $C_1$–$C_{20}$ alkyl, each having at least 2 alpha hydrogen atoms, or any or all of the pairs $R^1$ and $R^2$, $R^3$ and $R^4$, and $R^5$ and $R^6$, each pair selected independently, are –(CH$_2$)–$_4$ or –(CH$_2$)–$_2$CHY–(CH$_2$)–$_2$, wherein Y is hydrogen or methyl;

$R_f^1$ and $R_f^2$, each selected independently, are F, $C_{1\text{-}12}$ perfluoroalkyl, $C_{2\text{-}12}$ perfluoro(alkoxyalkyl), $C_{3\text{-}12}$ perfluoro(alkoxyalkoxyalkyl), $C_{4\text{-}12}$ perfluorocycloalkyl, or $XR_f^3$ wherein $R_f^3$ is $C_{1\text{-}12}$ perfluoroalkylene or $C_{4\text{-}12}$ perfluorocycloalkylene and X is Cl, Br or I, or $R_f^1$ and $R_f^2$ taken together are –(CF$_2$)–$_n$ wherein n is an integer and is 2 to 6; and Q is O or S.

Alkoxides wherein Q is O are preferred. More preferred are alkoxides wherein Q is O and (i) $R_f^1$ is linear $C_{1\text{-}9}$ perfluoroalkyl and $R_f^2$ is F; or (ii) $R_f^1$ and $R_f^2$ are each F or $CF_3$. Still more preferred are such alkoxides wherein $R^1$–$R^6$ are each $CH_3$, or the pairs $R^1$ and $R^2$, $R^3$ and $R^4$, $R^5$ and $R^6$ are each –(CH$_2$)–$_5$. Most preferred is the alkoxide wherein Q is O, $R_f^1$ and $R_f^2$ are each F, and $R^1$–$R^6$ are each $CH_3$.

The invention also resides in a process for the preparation of the above compounds. The process comprises contacting and reacting, in an inert solvent, the appropriate carbonyl or thiocarbonyl compound of the formula

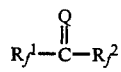

or epoxide or thioepoxide of the formula

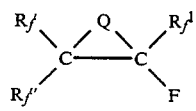

and the sulfonium salt of the formula $[(NR^1R^2)(NR^3R^4)(NR^5R^6)]S^{\oplus}(CH_3)_3SiF_2^{\ominus}$. $R_f'$ and $R_f''$ are defined as above for $R_f^1$ and $R_f^2$, respectively, except that the sum of the carbon atoms in $R_f'$ and $R_f'' \leq 11$, and all other symbols are as defined above.

Suitable solvents include any inert solvent, that is, a solvent that will dissolve the sulfonium salt without reacting with it. Examples include nitriles, such as acetonitrile, propionitrile, and benzonitrile, and amines, such as pyridine and quinoline.

The reaction can be carried out at $-100°$ to $100°$ C. Higher temperatures can be used, but generally provide no advantage. The preferred temperature range is $-80°$ to $50°$ C.

Ambient pressure is preferred for the reaction because of convenience, but either subatmospheric pressure or superatmospheric pressure is operable.

The reaction can be carried out with or without a solvent, although the presence of a solvent is preferred. When a solvent is employed, the fluorocarbonyl-, fluorothiocarbonyl-, fluoroepoxide or fluorothioepoxide compound and the difluorotrimethylsilicate salt should be present in concentrations of at least about 0.001 molar, preferably a least about 0.01 molar, more preferably at least about 0.1 molar. Either reactant can be in moderate excess, but best yields are achieved when the reactants are used in approximately equimolar amounts.

Either reactant can be added to the solvent first, followed by addition of the second reactant, or both reactants can be added to the solvent simultaneously. Alternatively, either or both reactants can be prepared in situ in the solvent, reaction then taking place when both reactants are present.

Isolation of the product can be accomplished by conventional means, for example, by evaporation of the reaction solvent at reduced pressure. Isolation is not always necessary, such as when the alkoxide or mercaptide is to be used as an intermediate.

Examples of alkoxides and mercaptides of the invention, and the reactants that can be used to prepare them, are shown in the following table.

| Reactants | Product |
|---|---|
| $ClCF_2-\overset{\overset{O}{\|\|}}{C}F$ and $[(CH_3)_2N]_3S^\oplus(CH_3)_3SiF_2^\ominus$ | $ClCF_2CF_2O^\ominus[(CH_3)_2N]_3S^\oplus$ |
| $(CF_2Cl)_2CO$ and $[(CH_3)_2N]_3S^\oplus(CH_3)_3SiF_2^\ominus$ | $(CF_2Cl)_2CFO^\ominus[(CH_3)_2N]_3S^\oplus$ |
| $(CF_3CF_2CF_2)_2CO$ and $[(CH_3)_2N]_3S^\oplus(CH_3)_3SiF_2^\ominus$ | $(CF_3CF_2CF_2)_2CFO^\ominus[(CH_3)_2N]_3S^\oplus$ |
| $\underset{\|}{CF_2}-\underset{\|}{CF}-\overset{\overset{O}{\|\|}}{C}F$ and $[(CH_3)_2N]_3S^\oplus(CH_3)_3SiF_2^\ominus$ (with $CF_2-CF_2$ ring) | $\underset{\|}{CF_2}-\underset{\|}{CF}-CF_2O^\ominus[(CH_3)_2N]_3S^\oplus$ (with $CF_2-CF_2$ ring) |
| $CF_3(CF_2)_{10}\overset{\overset{O}{\|\|}}{C}F$ and $[(CH_3)_2N]_3S^\oplus(CH_3)_3SiF_2^\ominus$ | $CF_3(CF_2)_{10}CF_2O^\ominus[(CH_3)_2N]_3S^\oplus$ |
| $F_2C$—$CFCl$ (cyclobutanone with $CF_2$, $CF_2$, $C=O$) and $[(CH_3)_2N]_3S^\oplus(CH_3)_3SiF_2^\ominus$ | $CF_2$—$CFCl$ (cyclobutane with $CF_2$, $CF_2$, $CFO^\ominus[(CH_3)_2N]_3S^\oplus$) |
| $CF_3CF_2CF_2O-\underset{\underset{F}{\|}}{\overset{\overset{CF_3}{\|}}{C}}-CF_2O-\underset{\underset{F}{\|}}{\overset{\overset{CF_3}{\|}}{C}}-\overset{\overset{O}{\|\|}}{C}F$ and $[(CH_3)_2N]_3S^\oplus(CH_3)_3SiF_2^\ominus$ (HFPO Trimer) | $CF_3CF_2CF_2O-\underset{\underset{F}{\|}}{\overset{\overset{CF_3}{\|}}{C}}-CF_2O-\underset{\underset{F}{\|}}{\overset{\overset{CF_3}{\|}}{C}}-CF_2O^\ominus[(CH_3)_2N]_3S^\oplus$ |
| $(CF_3)_2CF-\overset{\overset{O}{\|\|}}{C}CF_2CF_2CF_3$ and $\left[\bigcirc N\!\!-\!\!\right]_3 S^\oplus(CH_3)_3SiF_2^\ominus$ | $(CF_3)_2CF-\underset{\underset{F}{\|}}{\overset{\overset{CF_2CF_2CF_3}{\|}}{C}}-O^\ominus \left[\bigcirc N\!\!-\!\!\right]_3 S^\oplus$ |
| $ClCF_2\overset{\overset{S}{\|\|}}{C}F$ and $(Et_2N)_3S^\oplus(CH_3)_3SiF_2^\ominus$ | $ClCF_2CF_2S^\ominus \; ^\oplus S(NEt_2)_3$ |
| $CF_3CF_2-\overset{\overset{S}{\|\|}}{C}-CF_3$ and $\left[\bigcirc N\!\!-\!\!\right]_3 S^\oplus(CH_3)_3SiF_2^\ominus$ | $CF_3CF_2-\underset{\underset{F}{\|}}{\overset{\overset{CF_3}{\|}}{C}}-S^\ominus \; ^\oplus S-\left[\!\!-\!\!N\bigcirc\right]_3$ |
| $CF_3-\overset{\overset{S}{\|\|}}{C}F$ and $\left[\bigcirc N\!\!-\!\!\right]_3 S^\oplus(CH_3)_3SiF_2^\ominus$ | $CF_3CF_2S^\ominus \; ^\oplus S-\left[\!\!-\!\!N\bigcirc\right]_3$ |
| $CF_3CF-CF_2$ (epoxide, with O) and $[(CH_3)_2N]_3S^\oplus(CH_3)_3SiF_2^\ominus$ | $CF_3CF_2CF_2O^\ominus[(CH_3)_2N]_3S^\oplus$ |
| $CF_3$, $CF_3$ C—S—C with $CF_3$, $CF_3$ (and bridging S) and $[(CH_3)_2N]_3S^\oplus(CH_3)_3SiF_2^\ominus$ (hexafluoroacetone dimer) | $F-\underset{\underset{CF_3}{\|}}{\overset{\overset{CF_3}{\|}}{C}}-S^\ominus[(CH_3)_2N]_3S^\oplus$ |

In contrast to metal perfluoroalkoxides of the art, the sulfonium salts of the instant invention are very soluble in polar organic solvents without decomposition or reversion to a large equilibrium concentration of the carbonyl compound. The sulfonium salts of the instant invention can be fully characterized by NMR spectroscopy and are readily isolated from solution. The isolated salts are solids of surprising thermal stability. For example, $CF_3O^\ominus S^\oplus[N(CH_3)_2]_3$ is stable up to its melting point of 213° C.

The perfluoroalkoxide and mercaptide salts of this invention have utility as polymerization catalysts, for example, in polymerization reactions of the group transfer polymerization type disclosed: (1) by Webster et al. in *J. Am. Chem. Soc.*, 105, 5706 (1983); and (2) in U.S. Pat. Nos. 4,414,372; 4,417,034; 4,508,880; and 4,524,196, wherein such processes one or more selected $\alpha,\beta$-unsaturated compounds are contacted under polymerizing conditions with a selected silicon-, germanium-, or tin-containing initiator and a selected Lewis acid or anion catalyst. More specific details may be found in the patents, the disclosures of which are hereby incorporated by reference.

The perfluoroalkoxide and mercaptide salts of the invention are also useful as intermediates in the preparation of fluorine-containing organic compounds. As already indicated above, in contrast to many of the ionic metal salts of the corresponding fluoroalkoxides and mercaptides, the sulfonium salts are very soluble in many polar organic solvents without decomposition (or a large equilibrium concentration of fluoride ion). They show high anion reactivity, and can readily displace halogen (Cl, Br, I) or sulfonate groups ($FSO_3^\ominus$, $CF_3SO_3^\ominus$, $ArSO_3^\ominus$) from organic compounds to form fluoroalkyl ethers or fluoroalkyl sulfides. Many of the compounds that can be prepared from the sulfonium salts of the invention are useful as solvents, dielectric liquids, pharmaceuticals, and oxygen-carrying liquids for use in preparing artificial blood. Examples of fluoro-organic compounds which can be prepared from the sulfonium salts include methyl perfluoroisopropyl ether, a useful inhalation anaesthetic, and $CF_3CF_2CF_2O\text{-}[CF(CF_3)CF_2O]_2CH_3$, a solvent, a dielectric liquid, and an intermediate to the oxygen-carrying perfluoroether of the formula $CF_3CF_2CF_2O\text{-}[CF(CF_3)CF_2O]_2CF_3$. As disclosed in U.S. Pat. No. 3,549,711, perfluoroalkyl aliphatic and -alkaryl ethers, such as are prepared in Utility Examples A-F below, are useful as hydraulic fluids, including brake fluids, electrical insulators, oil and water repellants, and as monomers for the preparation of heat- and oxidation-resistant polymers.

In the following examples, temperatures are in degrees Celsius; $^1H$ NMR spectra are recorded in ppm downfield from tetramethylsilane standard; and $^{19}F$ NMR spectra are recorded in ppm downfield from Freon ®-11 internal standard. All reactants are known compounds which are commonly available. In Examples 1, 2 and 4 to 16, fluorotrimethylsilane is produced as a by-product.

EXAMPLE 1

Tris(dimethylamino)sulfonium Trifluoromethoxide

Carbonyl fluoride was passed into a solution of 23.23 g (0.084 mol) of tris(dimethylamino)sulfonium difluorotrimethylsilicate in 75 mL of dry acetonitrile cooled to 0°. The addition was stopped when no further exotherm was noted. The reaction mixture was warmed to 25° and then evaporated to dryness under reduced pressure to give 20.36 g (97%) of the trifluoromethoxide as a white solid: mp 214°-216°; $^1H$ NMR ($CD_3CN$, 25°) $\delta 2.88$ ppm (s); $^{19}F$ NMR (propionitrile, $-38.6°$) $\delta -20.3$ ppm (s).

EXAMPLE 2

Tris(piperidino)sulfonium Trifluoromethoxide

Carbonyl fluoride was passed into a solution of 15.0 g (0.038 mol) of tris(piperidino)sulfonium difluorotrimethylsilicate in 50 mL of acetonitrile at 25° until no more exotherm was noted. The reaction mixture warmed to 31°. Evaporation of the solvent under reduced pressure gave 12.2 g (88%) of the trifluoromethoxide as colorless crystals: mp 75°-79°; $^1H$ NMR ($CD_3CN$) $\delta 1.64$ ppm (m, 18H) and 3.21 ppm (m, 12H); $^{19}F$ NMR (propionitrile, $-80.6°$) $\delta -20.2$ ppm (s).

EXAMPLE 3

Tris(diethylamino)sulfonium Trifluoromethoxide

Diethylaminotrimethylsilane (29.06 g, 0.2 mol) was added dropwise to a solution of 12.5 mL (0.1 mol) of diethylaminosulfur trifluoride in 75 mL of acetonitrile at 25°. The reaction mixture was stirred overnight, and then saturated with carbonyl fluoride. Evaporation of the solvent under reduced pressure gave 30.3 g (91%) of the trifluoromethoxide: mp 85°-95°; $^1H$ NMR ($CD_3CN$) $\delta 1.21$ ppm (t, J=7H, 9H), 3.29 ppm (q, J=7 Hz, 6H); $^{19}F$ NMR ($CD_3CN$) $\delta -20.8$ ppm. Anal. Calcd. for $C_{13}H_{30}F_3N_3OS$: C, 46.83; H, 9.07; F, 17.07; N, 12.60. Found: C, 46.53; H, 9.17; F, 17.25; N, 12.55.

EXAMPLE 4

Tris(dimethylamino)sulfonium Pentafluoroethoxide

Trifluoroacetyl fluoride, 10.0 g (0.086 mol), was distilled into a solution of 18.5 g (0.067 mol) of tris(dimethylamino)sulfonium difluorotrimethylsilicate in 75 mL of acetonitrile cooled to 0°. The reaction mixture was warmed to 25° and then evaporated to dryness under reduced pressure to give 19.13 g (95%) of the pentafluoroethoxide as a white solid: mp 189°-191° after recrystallization from tetrahydrofuran (THF); $^1H$ NMR ($CD_3CN$) $\delta 2.88$ ppm (s); $^{19}F$ NMR (propionitrile, $-81.7°$) $\delta -82.7$ ppm (3F), $-32.7$ ppm (2F). Anal. Calcd. for $C_8H_{18}F_5N_3OS$: C, 32.10; H, 6.06. Found: C, 31.86; H, 6.62.

EXAMPLE 5

Tris(dimethylamino)sulfonium Heptafluoropropoxide

Pentafluoropropionyl fluoride, 18.0 g (0.108 mol), was distilled into a solution of tris(dimethylamino)sulfonium difluorotrimethylsilicate in 75 mL of acetonitrile cooled to $-10°$. The reaction mixture was warmed to 25° and then evaporated to dryness under reduced pressure to give 34.0 g (100%) of the heptafluoropropoxide as a white solid: mp 92°-102°; $^1H$ NMR ($CD_3CN$) $\delta 2.90$ ppm (s); $^{19}F$ NMR ($CD_3CN$) $\delta -30.3$ ppm (2F), $-81.0$ ppm (s, 3F) and $-124.8$ ppm (s, 2F). Anal. Calcd. for $C_9H_{18}F_7N_3OS$: C, 30.95; H, 5.19. Found: C, 31.37; H, 5.52.

EXAMPLE 6

Tris(dimethylamino)sulfonium Heptafluoroisopropoxide

Hexafluoroacetone, 9.18 mL (measured at −78°, 0.0918 mol), was slowly distilled into a stirred solution of 23.0 g (0.0834 mol) of tris(dimethylamino)sulfonium difluorotrimethylsilicate in 75 mL of acetonitrile cooled to 0°. The reaction mixture was allowed to warm to 25°, and then evaporated to dryness under reduced pressure to give 26.0 g (99% yield) of the heptafluoroisopropoxide as a white solid: mp 72°–77°; $^1$H NMR (CD$_3$CN) δ2.88 ppm (s); $^{19}$F NMR (CDCl$_3$, −39°) δ−74.5 ppm (septet, J=5 Hz, 1F) and −79.2 ppm (d, J=5 Hz, 6F).

EXAMPLE 7

Tris(dimethylamino)sulfonium 1,1,2,3,3,3-Hexafluoro-2-(trifluoromethyl)propoxide Perfluoroisobutyryl fluoride, 20.0 g (0.093 mol), was slowly distilled into a stirred solution of 23.0 g (0.0837 mol) of tris(dimethylamino)sulfonium difluorotrimethylsilicate in 75 mL acetonitrile cooled to −10°. The reaction mixture was warmed to 25° and then evaporated to dryness under reduced pressure to give 30.13 g (90% yield) of tris(dimethylamino)sulfonium 1,1,2,3,3,3-hexafluoro-2-(trifluoromethyl)propoxide: mp 93°–99°; $^1$H NMR (CD$_3$CN) δ2.90 ppm (s); $^{19}$F NMR (CD$_3$CN) δ−72.8 ppm (d, J=6 Hz, 6F), −179.5 ppm (septet, J=6 Hz, 1F), (signal due to —CF$_2$O too broad to determine). Anal. Calcd. for C$_{10}$H$_{18}$F$_9$N$_3$SO: C, 30.08; H, 4.54. Found: C, 30.00; H, 4.98.

EXAMPLE 8

Tris(dimethylamino)sulfonium Perfluorovaleroxide

Perfluorovaleryl fluoride, 26.6 g (0.1 mol), was distilled into a stirred solution of 25.0 g (0.091 mol) of tris(dimethyl)sulfonium difluorotrimethylsilicate in 75 mL of acetonitrile cooled to −10°. The reaction mixture was warmed to 25°, stirred for one h, and then evaporated to dryness under reduced pressure to give 37.4 g (92% yield) of the perfluorovaleroxide: mp 98°–102°; $^1$H NMR (CD$_3$CN) δ2.89 ppm (s); $^{19}$F NMR (CD$_3$CN) δ−30.3 ppm (2F), −80.7 ppm (m, 3F), −120.7 ppm (m, 2F), −122.2 ppm (m, 2F) and −125.6 ppm (m, 2F). Anal. Calcd. for C$_{11}$H$_{18}$F$_{11}$N$_3$OS: C, 29.40; H, 4.04. Found: C, 29.33 H, 4.35.

EXAMPLE 9

Tris(dimethylamino)sulfonium Perfluorocyclobutoxide

Perfluorocyclobutanone, 12.67 g (0.071 mol), was distilled into a stirred solution of 16.5 g (0.06 mol) of tris(dimethylamino)sulfonium difluorotrimethylsilicate in 75 mL of acetonitrile cooled to −10°. The reaction mixture was warmed to 25°, stirred for 1 h, and then evaporated to dryness under reduced pressure to give 21.3 g (98%) of the perfluorocyclobutoxide: mp 107°–111°; $^1$H NMR (CD$_3$CN) δ2.96 ppm (s); $^{19}$F NMR (CD$_3$CN) δ−131.9 ppm (m, 4F), −136.0 ppm (m, 1F), −136.0 ppm (m, 1F), −119.3 ppm (m, 2F), −66.8 ppm (m, 1F). Anal. Calcd. for C$_{10}$H$_{18}$F$_7$N$_3$OS: C, 33.24; H, 5.02; F, 36.80; N, 11.63. Found: C, 33.20; H, 4.97; F, 36.80; N, 11.55.

EXAMPLE 10

Tris(dimethylamino)sulfonium 1,1,2,3,3,3-Hexafluoro-2-(trifluoromethoxy)propoxide 2,3,3,3-Tetrafluoro-2-(trifluoromethoxy)propionyl fluoride, 18.6 g (0.08 mol), was distilled into a solution of 19.83 g (0.072 mol) of tris(dimethylamino)sulfonium difluorotrimethylsilicate in 75 mL of acetonitrile cooled to −10°. The reaction mixture was warmed to 25°, stirred for one h, and then evaporated to dryness under reduced pressure to give 27.5 g (92%) of the propoxide as a white solid: mp 49°–53°; $^1$H NMR (CD$_3$CN) δ2.90 ppm (s); $^{19}$F NMR (CD$_3$CN) δ−27.0 ppm (2F), −52.2 ppm (d, q, J=24, 3 Hz, 3F), −79.4 ppm (d, q, J=2, 3 Hz, 3F), −138.9 ppm (q, q, J=14, 2 Hz, 1F).

EXAMPLE 11

Tris(dimethylamino)sulfonium Trifluoromethanethiolate

Thiocarbonyl fluoride, 8.25 g (0.1 mol), was distilled into a stirred solution of 26.2 g (0.095 mol) of tris(dimethylamino)sulfonium difluorotrimethylsilicate in 75 mL of acetonitrile cooled to −40°. The reaction mixture was evaporated to dryness under reduced pressure to give 22.1 g (87%) of tris(dimethylamino)sulfonium trifluoromethanethiolate as a tan solid: mp 166°–169°; $^1$H NMR (CDCl$_3$) δ2.80 ppm (s); $^{19}$F NMR (CD$_3$CN) δ−6.53 ppm (s).

EXAMPLE 12

Tris(dimethylamino)sulfonium 1,2,2,2-Tetrafluoro-1-(trifluoromethyl)ethanethiolate 2,2,4,4-Tetrakis(trifluoromethyl)-1,3-dithietane, (hexafluorothioacetone dimer), 9.1 g (0.025 mol), was added dropwise to a stirred solution of 13.82 g (0.05 mol) of tris(dimethylamino)sulfonium difluorotrimethylsilicate in 40 mL of acetonitrile cooled to 0°. The reaction mixture was warmed to 25°, stirred for 2 h, and then evaporated to dryness under reduced pressure to give 16.28 g (89% yield) of the thiolate as a pale orange solid: $^1$H NMR (CD$_3$CN) δ3.88 ppm (s); $^{19}$F NMR (CD$_3$CN) δ−75.8 ppm (d, J=20 Hz, 6F) and −118.0 ppm (septet, J=20 Hz, 1F).

EXAMPLE 13

Tris(dimethylamino)sulfonium 1,1,2,3,3,3-Hexafluoro-2-(heptafluoropropoxy)propoxide A solution of tris(dimethylamino)sulfonium 1,1,2,3,3,3-hexafluoro-2-(heptafluoropropoxy)propoxide in benzonitrile was prepared by adding in one portion 10.0 g (0.03 mol) of 2,3,3,3,-tetrafluoro-2-(heptafluoropropoxy)propionyl fluoride to a stirred solution of 9.1 g (0.033 mol) of tris(dimethylamino)sulfonium difluorotrimethylsilicate in 30 mL of benzonitrile at 25°. The by-product fluorotrimethylsilane was distilled from the solution at reduced pressure. If desired, the product could be recovered from the solution by removal of the solvent.

EXAMPLE 14

Tris(dimethylamino)sulfonium 1,1,1,2,3,4,5,5,5-Nonafluoro-2,4-bis(trifluoromethyl)-3-pentyloxide Perfluorodiisopropyl ketone, 20.1 g (0.055 mol), was added dropwise to a solution of 13.8 g (0.05 mol) of tris(dimethylamino)sulfonium difluorotrimethylsilicate in 75 mL of acetonitrile cooled to 0°. The reaction mixture was stirred until it became homogeneous, and then was evaporated to dryness under reduced pressure. There was obtained 21.6 g (79%) of the sulfonium pentyloxide as a white solid: mp 38°–42°; $^1$H NMR (CD$_3$CN) δ2.85 ppm (s); $^{19}$F NMR (propionitrile, −80°) δ−34.0 ppm (½w=70 Hz, 1F), −68.8 ppm (½w=30 Hz, 12F) and −178.5 ppm (½w=36 Hz, 2F). A solution of this salt, stirred in benzonitrile at 25°, slowly decomposed to form the sulfonium salt of Example 7.

EXAMPLE 15

Tris(dimethylamino)sulfonium 1,1,1,2,2,3,4,4,5,5,5-Hendecafluoro-3-pentyloxide

Perfluoro-3-pentanone, 7.32 g (0.0275 mol), was added dropwise to a stirred solution of 6.92 g (0.025 mol) of tris(dimethylamino)sulfonium difluorotrimethylsilicate in 25 mL of acetonitrile at 0°. The reaction mixture was warmed to 25° and then evaporated to dryness to give 9.2 g (82%) of the sulfonium pentyloxide as a white sold: mp 70°–72°; $^1$H NMR (CDCl$_3$) δ3.86 ppm (s); $^{19}$F NMR (CDCl$_3$) δ−74.8 ppm (very broad, 1F), −78.9 ppm (s, ½w=4.5 Hz, 6F), −122.1 ppm (s, ½w=7 Hz, 4F). Anal. Calcd. for C$_{11}$H$_{18}$F$_{11}$N$_3$OS: C, 29.40; H, 4.04; F, 46.51; N, 9.35. Found: C, 29.28; H, 4.18; F, 46.23; N, 9.50.

EXAMPLE 16

Tris(dimethylamino)sulfonium 2-Chloro-1,2-2-trifluoro-1-(trifluoromethyl)ethoxide Chloropentafluoroacetone, 10.0 g (0.055 mol), was distilled into a solution of 13.7 g (0.05 mol) of tris(dimethylamino)sulfonium difluorotrimethylsilicate in 75 mL of acetonitrile cooled to 0°. The reaction mixture was warmed to 25° and then evaporated to dryness under reduced pressure to give 16.92 g (93%) of the ethoxide as a white solid: mp 68°–72°; $^{19}$F NMR (CD$_3$CN) δ−64.2 ppm (q, J=10 Hz, 2F), −78.6 ppm (t, J=10 Hz, 3F), −80.9 ppm (broad, 1F); $^1$H NMR (CD$_3$CN) δ3.86 ppm (s). Anal. Calcd. for C$_9$H$_{18}$ClF$_6$N$_3$OS: C, 29.55; H, 4.96; F, 31.17; N, 11.49. Found: C, 29.73; H, 5.06; F, 30.98; N, 11.39.

EXAMPLE 17

Tris(dimethylamino)sulfonium Heptafluoropropoxide

A solution of tris(dimethylamino)sulfonium difluorotrimethylsilicate (9.63 g, 35 mmol) in THF (60 mL) at −78° was treated slowly with hexafluoropropene oxide (6.39 g, 39 mmol). The mixture was stirred at −78° for 0.5 h, then allowed to warm to 25°. Evaporation provided 12.2 g of solid which was recrystallized from THF/ether to remove a small amount of yellow impurity. $^1$H NMR (CD$_3$CN): 2.95 (s). $^{19}$F NMR (CD$_3$CN/F$_{11}$): δ−80.62 (s, CF$_3$) and −124.58 (s, CF$_2$) with minor contaminant signals at −81.90 (s) and −118.18 (s). The spectrum matched that for the alkoxide obtained from Example 5.

EXAMPLE 18

Polymerization of Methylmethacrylate with TAS CF$_3$S Catalyst

A solution of [(1-methoxy-2-methyl-1-propenyl)oxy]-trimethylsilane (0.70 g) and methyl methacrylate (5.0 mL) in THF (25 mL) at room temperature was treated with a solution of TAS trifluorothiomethoxide (25 mg) in acetonitrile (0.2 mL). The temperature increased to 43°. After cooling to room temperature, evaporation of solvent provided 6.13 g of light tan product comprising poly(methylmethacrylate).

Following are examples which demonstrate the utility of the compounds of the invention.

EXAMPLE A

Benzyl Trifluoromethyl Ether

Benzyl bromide, 12.47 g (0.073 mol), was added dropwise at 25° to a solution of 0.081 mol of tris(dimethylamino)sulfonium trifluoromethoxide (prepared as in Example 1) in 75 mL of acetonitrile. The reaction mixture was stirred at 25° for 18 h and then poured into ice-water. The aqueous mixture was extracted with ether, and the ether extracts were washed with water, dried (MgSO$_4$), and distilled to give 10.55 g (85%) of benzyl trifluoromethyl ether as a colorless oil: bp 45°–46° (18 mm); $^1$H NMR (CDCl$_3$) δ4.93 ppm (s, 2H), 7.33 ppm (s, 5H); $^{19}$F NMR (CDCl$_3$) δ−60.6 ppm (s). Anal. Calcd. for C$_8$H$_7$F$_3$O: C, 54.55; H, 4.01; F, 32.36. Found: C, 54.76; H, 4.04; F, 32.51.

EXAMPLE B

α-Trifluoromethoxyacetophenone

α-Bromoacetophenone, 13.61 g (0.068 mol), was added dropwise at 25° to a solution of 0.076 mol of tris(dimethylamino)sulfonium trifluoromethoxide (prepared as in Example 1) in 75 mL of acetonitrile. The reaction mixture was stirred for 3 days and then poured into ice-water. The aqueous mixture was extracted with ether, and the ether extracts were washed with water, dried (MgSO$_4$), and distilled to give α-trifluoromethoxyacetophenone as a colorless liquid: bp 64°–65° (0.8 mm); $^1$H NMR (CDCl$_3$) δ5.15 ppm (s, 2H), 7.50 ppm (m, 3H), 7.85 ppm (m, 2H); $^{19}$F NMR (CDCl$_3$) δ−61.5 ppm(s).

EXAMPLE C

Trifluoromethyl Diphenylmethyl Ether

Bromodiphenylmethane, 20.7 g (0.084 mol), was added portionwise at 25° to a stirred solution of 0.093 mole of tris(dimethylamino)sulfonium trifluoromethoxide (prepared as in Example 1) in 75 mL of acetonitrile. The reaction mixture was stirred for 18 h and then poured into water. The aqueous mixture was extracted with ether, and the ether extracts were washed with water, dried (MgSO$_4$), and then distilled to give 8.34 g of trifluoromethyl diphenylmethyl ether as a colorless oil: bp 83.3° (0.7 mm); $^1$H NMR (CDCl$_3$) δ6.17 ppm (s, 1H), 7.27 ppm (m, 10H); $^{19}$F NMR (CDCl$_3$) δ−58.4 ppm (s). Anal. Calcd. for C$_{14}$H$_{11}$F$_3$O: C, 66.66; H, 4.40; F, 22.60. Found: C, 66.82; H, 4.57; F, 22.39.

EXAMPLE D

Methyl 1,1,2,3,3,3-Hexafluoro-2-(trifluoromethoxy)propyl Ether

Methyl trifluoromethanesulfonate, 8.53 g (0.052 mol), was added dropwise to a stirred solution of 23.0 g (0.055 mol) of tris(dimethylamino)sulfonium 1,1,2,3,3,3-hexafluoro-2-(trifluoromethoxy)propoxide (prepared as in Example 10) in 50 mL of benzonitrile at 25°. The reaction mixture warmed spontaneously to 40°. After stirring for one h at ambient temperature the more volatile portion of the reaction mixture was distilled out at reduced pressure, and then redistilled at atmospheric pressure to give 8.96 g (65%) of the ether as a colorless liquid: bp 64.4°; $^1$H NMR (CDCl$_3$) δ3.71 ppm (s); $^{19}$F NMR (CDCl$_3$) δ −54.1 ppm (m, 3F), −80.8 ppm (m, 3F), δ −88.6 ppm (m, 2F) and −146.1 ppm (m, 1F). Anal. Calcd. for C$_5$H$_3$F$_9$O$_2$: C, 22.57; H, 1.14; F, 64.27. Found: C, 22.63; H, 1.17; F, 63.67.

EXAMPLE E

Methyl 1,1,2,3,3,3-Hexafluoro-2-(heptafluoropropoxy)propyl Ether

Methyl trifluoromethanesulfonate, 4.92 g (0.03 mol), was added dropwise to 0.03 mol of tris(dimethylamino)-sulfonium 1,1,2,3,3,3-hexafluoro-2-(heptafluoropropoxy)propoxide (prepared as in Example 13) in 30 mL of benzonitrile. The reaction mixture was stirred for 1.5 h and then the more volatile portion of the reaction mixture was distilled out at reduced pressure and redistilled at atmospheric pressure to give 6.39 g (58%) of methyl 1,1,2,3,3,3-hexafluoro-2-(heptafluoropropoxy)propyl ether as a colorless liquid: bp 94°–96°; $^1$H NMR (CDCl$_3$) δ3.70 ppm (s); $^{19}$F NMR (CD$_3$Cl) δ −81.0 ppm (m, 3F), −82.1 ppm (m, 3F), −82.4 ppm (m, 2F), −88.7 ppm (m, 2F), −130.3 ppm (m, 2F) and −144.8 ppm (m, 1F). Anal. Calcd. for C$_7$H$_3$F$_{13}$O$_2$: C, 22.96; H, 0.82. Found: C, 22.95; H, 0.78.

EXAMPLE F

Benzyl 1,1,2,3,3,3-Hexafluoro-2-(trifluoromethyl)propyl Ether

Benzyl bromide, 10.62 g (0.0621 mol), was added dropwise to a solution of 27.5 g (0.069 mol) of tris(dimethylamino)sulfonium 1,1,2,3,3,3-hexafluoro-2-(trifluoromethyl)propoxide (prepared as in Example 7) in 50 mL of acetonitrile at 25°. The reaction mixture was stirred for 2 h and then poured into water. The aqueous mixture was extracted with ether, and the ether extracts were washed with water, dried (MgSO$_4$), and distilled to give benzyl 1,1,2,3,3,3-hexafluoro-2-(trifluoromethyl)propyl ether as a colorless liquid: bp 86°–87° (36 mm); $^{19}$F NMR (CDCl$_3$) δ −73.9 ppm (t, d, J=9, 6 Hz, 6F), −79.2 ppm (d, septet, J=9, 9 Hz, 2F), and −187.7 ppm (t, septet, J=9, 6 Hz, 1F). Anal. Calcd. for C$_{11}$H$_7$F$_9$O: C, 40.50; H, 2.16. Found: C, 40.69; H, 2.29.

EXAMPLE G

Benzyl Trifluoromethyl Sulfide

Benzyl bromide, 16.2 g (0.095 mol), was added dropwise at 25° to 0.11 mol of tris(dimethylamino)sulfonium trifluoromethanethiolate (prepared as in Example 11) in 75 mL of acetonitrile. The reaction mixture was stirred one h and then poured into water. The aqueous mixture was extracted with ether, and the ether extracts were washed with water, dried (MgSO$_4$), and distilled to give 15.1 g (82%) of benzyl trifluoromethyl sulfide as a colorless liquid: bp 55° (12 mm); $^1$H NMR (CDCl$_3$) δ4.08 ppm (s, 2H), 7.33 ppm (s, 5H); $^{19}$F NMR (CDCl$_3$) δ −42.5 ppm (s).

EXAMPLE H

Benzyl Heptafluoroisopropyl Sulfide

Benzyl bromide, 16.76 g (0.098 mol), was added dropwise at 25° to a solution of 0.098 mole of tris(dimethylamino)sulfonium 1,2,2,2-tetrafluoro-1-(trifluoromethyl)ethanethiolate (prepared as in Example 12) in 125 mL of acetonitrile. The reaction mixture was stirred for 18 h and then poured into 500 mL of ice-water. The aqueous mixture was extracted with ether, and the ether extracts were washed with water, dried (MgSO$_4$) and distilled to give 21.31 g (75% yield) of benzyl heptafluoroisopropyl sulfide as a pale yellow liquid: bp 70°–71° (10 mm); $^1$H NMR (CDCl$_3$) δ4.09 ppm (s, 2H) and 7.27 ppm (s, 5H); $^{19}$F NMR (CDCl$_3$) δ −75.2 ppm (d, J=11 Hz, 6F) and −162.6 ppm (septet, J=11 Hz, 1F). Anal. Calcd. for C$_{10}$H$_7$F$_7$S: C, 41.10; H, 2.41; F, 45.51. Found: C, 40.89; H, 2.45; F, 45.27.

EXAMPLE I

Polymerization of Methyl Methacrylate with Tris(dimethylamino)sulfonium Trifluoromethoxide A solution of 4.0 mg of tris(dimethylamino)sulfonium trifluoromethoxide (prepared as in Example 1) in 20 μL of acetonitrile was added to a solution of 0.40 g of methyl trimethylsilyl dimethylketene acetal in 25 mL of tetrahydrofuran under argon cooled to 12°. Methyl methacrylate (5.0 mL) was added slowly by syringe, keeping the temperature below 40°. After the exotherm subsided, the mixture was stirred for 0.5 h and another 5.0 mL portion of methyl methacrylate was added as before. A third portion of monomer was added in a similar fashion, maintaining the exothermic reaction below 40°. The product consisted of poly(methylmethacrylate). The trifluoromethoxide thus serves as a catalyst for the group transfer polymerization process disclosed in U.S. Pat. Nos. 4,414,372 and 4,417,034, giving living polymer.

BEST MODE FOR CARRYING OUT THE INVENTION

The best mode presently contemplated is represented by Examples 1–6 and 8, especially Examples 1, 2 and 6.

INDUSTRIAL APPLICABILITY

The compounds of the invention are especially useful as intermediates in the preparation of fluorine-containing compounds which find numerous commercial applications, such as solvents, dielectric fluids, hydraulic fluids, pharmaceuticals and oil and water repellants.

Although the preferred embodiments of the invention have been illustrated and described, it is to be understood that there is no intent to limit the invention to the precise constructions herein disclosed, and the right is reserved to all changes and modifications coming within the scope of the invention as defined in the appended claims.

We claim:

1. Process of polymerizing one or more α,β-unsaturated compounds of the formulas CH$_2$=C(Y)X and

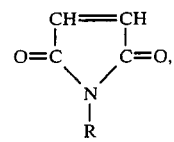

and mixtures thereof, wherein:

X is —CN, —CH=CHC(O)X' or —C(O)X';

Y is —H, —CH$_3$, —CN or —CO$_2$R, provided, however, when X is —CH=CHC(O)X', Y is —H or —CH$_3$;

X' is $-OSi(R^1)_3$, $-R$, $-OR$ or $-NR'R''$;

each $R^1$, independently, is a hydrocarbyl radical which is an aliphatic, alicyclic, aromatic or mixed aliphatic-aromatic radical containing up to 20 carbon atoms or $-H$, provided that at least one $R^1$ group is not $-H$;

R is:
  (a) a hydrocarbyl radical which is an aliphatic, alicyclic, aromatic or mixed aliphatic-aromatic radical containing up to 20 carbon atoms;
  (b) a polymeric radical containing at least 20 carbon atoms;
  (c) a radical of (a) or (b) containing one or more ether oxygen atoms within aliphatic segments thereof;
  (d) a radical of (a), (b) or (c) containing one or more functional substituents that are unreactive under polymerizing conditions; or
  (e) a radical of (a), (b), (c) or (d) containing one or more reactive substituents of the formula $-Z'(O)-C-C(Y^1)=CH_2$ wherein $Y^1$ is $-H$ or $-CH_3$ and $Z'$ is O or $NR'$ wherein $R'$ is as defined below; and each of $R'$ and $R''$ is independently selected from $C_{1-4}$ alkyl, the process comprising contacting said compounds under group transfer polymerizing conditions in the presence of a suitable silicon-, germanium- or tin-containing initiator and as the catalyst the tris(disubstituted amino)sulfonium perfluoroalkoxide of the formula

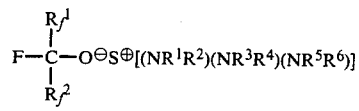

wherein
$R^1$ through $R^6$, each selected independently, are $C_{1-20}$ alkyl, each having at least 2 alpha hydrogen atoms, or any or all of the pairs $R^1$ and $R^2$, $R^3$ and $R^4$, and $R^5$ and $R^6$, each pair selected independently, are $-(CH_2)_4-$ or $-(CH_2)_2CHY-(CH_2)_2-$, wherein Y is hydrogen or methyl; and $R_f^1$ and $R_f^2$, each selected independently, are F, $C_{1-12}$ perfluoroalkyl, $C_{2-12}$ perfluoro(alkoxyalkyl), $C_{3-12}$ perfluoro(alkoxyalkoxyalkyl), $C_{4-12}$ perfluorocycloalkyl, or $XR_f^3$ wherein $R_f^3$ is $C_{1-12}$ perfluoroalkylene or $C_{4-12}$ perfluorocycloalkylene and X is Cl, Br or I, or $R_f^1$ and $R_f^2$ taken together are $-CF_2-_n$ wherein n is an integer and is 2 to 6.

2. Process of claim 1 wherein $R_f^1$ is linear $C_{1-9}$ perfluoroalkyl and $R_f^2$ is F.

3. Process of claim 2 wherein each of $R^1-R^6$ is $CH_3$.

4. Process of claim 1 wherein each of $R_f^1$ and $R_f^2$ is F.

5. Process of claim 4 wherein each of $R^1-R^6$ is $CH_3$.

6. Process of claim 5 wherein the $\alpha,\beta$-unsaturated compound is methyl methacrylate.

* * * * *

UNITED STATES PATENT AND TRADEMARK OFFICE
CERTIFICATE OF CORRECTION

PATENT NO. : 4,621,125

DATED : November 4, 1986

INVENTOR(S) : William Brown Farnham and William Joseph Middleton

It is certified that error appears in the above—identified patent and that said Letters Patent is hereby corrected as shown below:

Claim 1, next to last line, " $-CF_2-_n$ " should be -- $(CF_2)_n$ --.

Signed and Sealed this

Twenty-fourth Day of March, 1987

Attest:

DONALD J. QUIGG

Attesting Officer     Commissioner of Patents and Trademarks